(12) United States Patent
Hell (10) Patent No.: US 9,024,279 B2
(45) Date of Patent: May 5, 2015

(54) DETERMINING THE DISTRIBUTION OF A SUBSTANCE BY SCANNING WITH A MEASURING FRONT

(71) Applicant: Max-Planck-Gesellschaft zur Foerderung der Wissenschaften e.V., Munich (DE)

(72) Inventor: Stefan W. Hell, Goettingen (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 276 days.

(21) Appl. No.: 13/657,071

(22) Filed: Oct. 22, 2012

(65) Prior Publication Data
US 2013/0037729 A1    Feb. 14, 2013

Related U.S. Application Data

(63) Continuation-in-part of application No. PCT/EP2011/056058, filed on Apr. 15, 2011.

(30) Foreign Application Priority Data

Apr. 22, 2010  (DE) .......................... 10 2010 028 138

(51) Int. Cl.
*F21V 9/16* (2006.01)
*G01N 21/64* (2006.01)

(52) U.S. Cl.
CPC ........ *G01N 21/6458* (2013.01); *G01N 21/6428* (2013.01)

(58) Field of Classification Search
CPC ................. G01N 21/6458; G01N 2021/6421; G01N 2021/6419
USPC ..................................................... 250/459.1
See application file for complete search history.

(56) References Cited

U.S. PATENT DOCUMENTS

| 7,485,875 B2 | 2/2009 | Wolleschensky et al. |
| 7,539,115 B2 | 5/2009 | Hell |

(Continued)

FOREIGN PATENT DOCUMENTS

| DE | 100 56 382 A1 | 5/2002 |
| DE | 101 05 391 A1 | 8/2002 |

(Continued)

OTHER PUBLICATIONS

"Supraresolution imaging in brain slices using Stimulated-Emission Depletion Two-Photon Laser Scanning Microscopy", Neuron 63, 420-437 (2009), to Ding et al.*

(Continued)

*Primary Examiner* — David J Makiya
*Assistant Examiner* — Kenneth J Malkowski
(74) *Attorney, Agent, or Firm* — Thomas | Horstemeyer, LLP (57) ABSTRACT

For determining the distribution of a substance, a measuring front is formed of a first and a second optical signal. Intensities of the first and second optical signals, over a depth of the measuring front which is smaller than the diffraction limit at the wavelengths of the first and second optical signals, increase so steeply that a portion of the substance in a measurement state in which a measurement signal is available from the substance increases from essentially zero due to transferring the substance by means of the first optical signal into the measurement state, and decreases to essentially zero again due to transferring the substance by means of the second optical signal back out of the measurement state. The measuring front is moved over a measurement region. The measurement signal is recorded for different positions of the measuring front in the measurement region and assigned to these positions.

43 Claims, 3 Drawing Sheets

(56) References Cited

U.S. PATENT DOCUMENTS

| | | |
|---|---|---|
| 2002/0063220 A1 | 5/2002 | Engelhardt et al. |
| 2002/0104961 A1 | 8/2002 | Hoffman |
| 2007/0023686 A1 | 2/2007 | Wolleschensky et al. |
| 2007/0206278 A1 | 9/2007 | Dyba et al. |
| 2008/0007730 A1 | 1/2008 | Kempe |
| 2009/0242801 A1* | 10/2009 | Engelhardt et al. ........ 250/459.1 |
| 2009/0250632 A1 | 10/2009 | Kempe et al. |
| 2009/0289184 A1 | 11/2009 | Deininger et al. |
| 2009/0294694 A1 | 12/2009 | Lippert |
| 2010/0008394 A1 | 1/2010 | Miteva et al. |
| 2010/0140506 A1 | 6/2010 | Eggeling et al. |
| 2010/0176307 A1 | 7/2010 | Hell et al. |
| 2011/0036996 A1 | 2/2011 | Wolleschensky et al. |
| 2011/0182529 A1 | 7/2011 | Kempe et al. |
| 2011/0284767 A1 | 11/2011 | Wolleschensky et al. |

FOREIGN PATENT DOCUMENTS

| | | |
|---|---|---|
| DE | 103 25 459 A1 | 11/2004 |
| DE | 10 2005 034 443 A1 | 2/2007 |
| DE | 10 2006 009 831 A1 | 9/2007 |
| DE | 10 2006 011 176 A1 | 9/2007 |
| DE | 10 2006 026 204 A1 | 12/2007 |
| DE | 10 2006 046 369 A1 | 4/2008 |
| DE | 10 2006 047 912 A1 | 4/2008 |
| DE | 10 2007 033 737 A1 | 1/2009 |
| DE | 10 2007 039 111 A1 | 2/2009 |
| DE | 10 2008 009 216 A1 | 8/2009 |
| DE | 10 2008 011 993 A1 | 9/2009 |
| DE | 10 2008 023 438 A1 | 12/2009 |
| DE | 10 2008 049 878 A1 | 4/2010 |
| DE | 10 2008 054 317 A1 | 5/2010 |
| DE | 10 2009 008 646 A1 | 8/2010 |
| WO | 2009/106602 A1 | 9/2009 |

OTHER PUBLICATIONS

Hell, S. W.: "Microscopy and its focal switch", Nature Methods, vol. 6 (2009), p. 28, right column, § 4.

Giske A. et al.: "New developments in STED Microscopy", Proceedings of the SPIE—The International Society for Optical Engineering SPIE-The International Society for Optical Engineering USA, vol. 7578, Jan. 24, 2010—Jan. 28, 2010, XP-002653265, ISSN: 0277-786X.

Bretschneider S. et al.: "Breaking the diffraction barrier in fluorescence microscopy by optical shelving", Physical Review Letters APS USA, vol. 98, No. 21, May 25, 2007, pp. 218103/1-4, XP-002653266, ISSN: 0031-9007.

Tinnefeld P. et al.: "Optical switches: Key molecules for improved fluorescence imaging and tracking with high optical resolution", Progress in Biomedical Optics and Imaging—Proceedings of SPIE—Biophotonics 2007: Optics in Life Science 2007 SPIE US, vol. 6633, 2007, XP-002653267.

PCT International Preliminary Report on patentability and Written Opinion in co-pending related PCT Application No. PCT/EP2011/056058, mailed Oct. 23, 2012.

* cited by examiner

DETERMINING THE DISTRIBUTION OF A SUBSTANCE BY SCANNING WITH A MEASURING FRONT

RELATED APPLICATIONS

The present application is a continuation-in-part (CIP) of international patent application PCT/EP2011/056058 filed on Apr. 15, 2011 and entitled "Determination of the Distribution of a Substance by Scanning with a Measuring Front". The international application claims priority to German patent application DE 10 2010 028 138.7, filed on Apr. 22, 2010 and entitled "Bestimmen der Verteilung einer Substanz durch Abtasten mit einer Messfront".

FIELD OF THE INVENTION

The present invention relates to a method of determining the distribution of a substance in a measurement region.

The distribution of the substance in the measurement region may be due to a structure in a sample marked with the substance, and the method may be carried out to image the structure.

In another embodiment, information may be encoded in a data carrier by means of the distribution of the substance. In this case, the method may be used to read this information.

Further, the present invention relates to a method of locally initiating a conversion of a substance in a conversion region.

BACKGROUND

STED and GSD fluorescence light microscopy are known as methods of providing a spatial resolution surpassing the diffraction limit in imaging a structure in a sample marked with a fluorescent dye. In STED fluorescence light microscopy, a measurement volume out of which the fluorescence light is spontaneously emitted from the sample is reduced as compared to the diffraction-limited dimensions of a focused beam of excitation light in that the intensity distribution of the excitation light beam in the sample is superimposed with an intensity distribution of stimulation light. The intensity distribution of the stimulation light has a zero point at a measurement point, and adjacent to the measurement point it has such a high intensity that the fluorescent dye is transferred by stimulated emission out of its electronically excited fluorescent state into an energetically lower non-fluorescent electronic state. The measurement point is thus framed by an area out of which no spontaneously emitted fluorescence light may origin due to the intensity of the stimulation light.

In GSD fluorescence light microscopy, the spatial limitation of the area of the sample out of which the spontaneously emitted fluorescence light may origin is achieved in that the fluorescent dye outside the measurement point is transferred into a dark state either directly out of its ground state or out of an electronically excited fluorescent state by means of an optical signal. The fluorescent dye does not get back out of this dark state at least as long as the same measurement point is measured so that no excitation of the fluorescent dye for a spontaneous emission of fluorescence light is possible due to the depletion of the ground state of the fluorescent dye. Here, the intensity distribution of the optical signal depleting the ground state of the fluorescent dye is basically the same as that one of the stimulation light in STED fluorescence light microscopy. This means that when scanning a sample with the actual measurement point each molecule of the fluorescent dye—prior to being reached by the measurement point—is subjected to relevant intensities of the excitation light and of the stimulation light or the optical signal used for depleting the ground state of the fluorescent dye, and has thus already undergone a number of transfer cycles. This number of transfer cycles is associated with a considerable danger of at least temporarily bleaching the fluorescent dye. This danger may be reduced by interrupting the respective optical signal. This, however, elongates the duration of the measurement. Although a lot of even very sensitive fluorescent dyes may return out of their dark state into their ground state excitable for fluorescence at least a few times, they are not suited for high spatial resolution STED and GSD fluorescence light microscopy for the above reasons.

In so-called RESOLFT fluorescence light microscopy, switchable fluorescent dyes are used which are transferable between conformation states with different fluorescence properties. These switchable fluorescent dyes allow to work with lower high light intensities and thus reduce the danger of bleaching the fluorescence dye when applying the principles of STED and GSD fluorescence light microscopy. The conformation states of the switchable fluorescent dyes display a longer lifetime than the electronic states which are the only states usable with simple fluorescent dyes in STED and GSD fluorescence light microscopy. The general problem that an individual molecule of the fluorescent dye has already been subjected to considerable light intensities and thus to a plurality of changes of state within short term prior to be reached by the actual measurement point, however, is still present. Additionally, the selection of switchable fluorescent dyes is still limited despite considerable development efforts, and even many of the available switchable fluorescent dyes are not as often switchable without damages as needed in STED or GSD fluorescence light microscopy when the measurement point gets closer to an individual dye molecule. Thus, the number of possible changes of state of the fluorescent dyes within short term is the limiting factor with all methods of high resolution light scanning microscopy known up to now (see Hell, S. W., "Microscopy and its focal switch", Nature Methods, Vo. 6 (2009), page 28, right column, §4).

Besides the methods providing a spatial resolution overcoming the diffraction limit in imaging a structure marked with a fluorescent dye in a sample in which the spatial area of the sample out of which the measurement signal may origin is limited, there are methods known as PALM and STORM in which purposefully only a small fraction of the molecules of the substance marking the structure is activated into an active state and excited in this active state for the emission of fluorescence light with excitation light. The fraction of the molecules in the active state is kept so small that the fluorescence light from the sample may be assigned to individual molecules of the fluorescent dye. Thus, via the relative intensity distribution of the fluorescence light from one individual fluorescent molecule over several pixels of a two-dimensional detector array recording the fluorescence light, the position of the fluorescent molecule in the sample may be determined at a spatial resolution beyond the diffraction limit. Here, however, it is a precondition that a number of fluorescence light photons emitted by the individual fluorescent molecule which is sufficient from a statistical point of view reaches the detector. This does not only prolong the measurement time but also requires that the fluorescent dye molecules are at all suited for emitting a larger number of fluorescence light photons before they return in their non-active state or before they are transferred into a further state in which they are not excited for fluorescence by the excitation light. In this way, the number of practically available activatable fluorescent dyes which may in principle be the same switchable fluorescent dyes which are used in the RESOLFT technique is strongly limited.

A technique known as GSDIM is inverse as compared to PALM and may be applied with common fluorescent dyes. The inversion means that so many molecules of the fluorescent dye are temporarily deactivated into a dark state in GSDIM that the remaining fluorescent dye molecules are detectable individually. In this technique, however, the molecules of the fluorescent dye are all subjected to high light intensities and thus, prior to their actual measurement, to a correspondingly high number of changes of state to transfer them into their dark state and to keep their majority in this dark state.

DE 103 25 459 A1 discloses a method of forming a spatial structure at a spatial resolution beyond the diffraction limit. In this method, a substance is only left in a reactive state in a writing area which corresponds to an intensity minimum of an optical signal. Outside the writing area, the substance is transferred into a non-reactive state by means of the optical signal. When the substance so far as being in its reactive state is converted by means of a physical signal, this conversion is limited to the writing area. Also in this case, the substance is already subjected to very high light intensities and correspondingly many changes of state within short time when the writing area approaches a certain point of a substrate.

A further method of determining the distribution of a substance in a measurement region and a scanning light microscope are known from DE 10 1005 034 443 A1. Here, a luminescent sample is only subjected to excitation radiation of a single wavelength to avoid the effort associated with other methods for enhancing the spatial resolution. By means of the excitation radiation, the sample is transferred out of a first luminescence state in which the excitation for emission of luminescence radiation increases with increasing excitation radiation power up to a maximum value which corresponds to an excitation radiation power threshold value into a second luminescence state in which the sample displays a reduced excitability for emission of the luminescence radiation as compared to the first state. By irradiating the excitation radiation at a power above the threshold value the sample is transferred into the second state. In that the irradiation of excitation radiation takes place with an excitation radiation distribution which comprises a local power maximum above the threshold value and a local power minimum below the threshold value, the sample is transferred into the first state within partial areas and into the second state within adjacent partial areas. As a result, an image of the luminescent sample comprises sample areas in the first state and sample areas in the second state wherein predominantly sample areas in the first state contribute to the image of the luminescent sample and wherein the image has an increased spatial resolution as compared to the excitation radiation distribution. Particularly, the sample may be illuminated with the excitation radiation being focused to a line, wherein the power of the excitation radiation is, for example, sinusoidally modulated along the line so that the power is above the threshold value in some line sections and below the threshold value in some other line sections. Then, a scanning movement is made perpendicular to and along the line; and a detector for the luminescence radiation is a suitable high resolution line detector. The known method and the known microscope are depending on luminescent substances which comprise the described behavior with regard to an increasing excitation radiation power at a single wavelength. This is neither the case for all fluorescent dyes nor for all other luminescent substances nor for all so-called switchable fluorescence dyes, switchable fluorescent proteins and activatable luminescent particles.

There still is a need for a method of and a scanning light microscope for determining the distribution of a substance in a measurement region at a high spatial resolution in which fewer limitations with regard to the substances apply. Further, in a method of locally initiating a conversion of a substance in a conversion area, the substance, prior to initiating its conversion with a physical signal, should only be subjected to a low number of changes of state.

SUMMARY OF THE INVENTION

The present invention relates to a method of determining the distribution of a substance in a measurement region, the substance being transferable, by means of a first optical signal, (a) out of a first state in which no measurement signal is available from the substance into a measurement state in which a measurement signal is available from the substance, and, by means of a second optical signal, (b) into one of the first state and a second state in which no measurement signal is available from the substance. The method comprises forming a measuring front of the first and second optical signals in the measurement region, wherein intensities of the first and second optical signals, over a depth of the measuring front which is smaller than the diffraction limit at the wavelengths of the first and second optical signal, increase so steeply that a portion of the substance in the measurement state over the depth of the measuring front increases from essentially zero due to transferring the substance by means of the first optical signal (a) out of the first state into the measurement state, and decreases to essentially zero again due to transferring the substance by means of the second optical signal (b) into the one of the first and second states. The method further comprises moving the measuring front over the measurement region in a direction opposite to the increase of the intensities of the first and second optical signals over the depth of the measuring front; at least recording the measurement signal emitted out of the measuring front for different positions of the measuring front in the measurement region; and assigning the recorded measurement signal to the corresponding position of the measuring front in the measurement region. In the method, the first and second optical signals have different wavelengths, and the intensities of both the first and second optical signals in the measurement region are structured in a same way.

The present invention further relates to a scanning light microscope for determining the distribution of a substance in a measurement region. The scanning light microscope comprises a light source configured to provide first and second optical signals of different wavelength; optics configured to form a measuring front of the first and second optical signals in the measurement region; a scanner configured to move the measuring front with regard to the measurement region; and a detector configured to at least record a distribution of the measurement signal emitted out of the measuring front with spatial resolution along the measuring front. In the light microscope, the optics comprise same optical elements for structuring intensity distributions of the first and second optical signals in the over the measuring front.

The present invention further relates to a method of locally initiating a conversion of a substance in a conversion region, the substance being transferable by means of a first optical signal (a) out of first non-reactive state in which the conversion can not be initiated by a physical signal into a reactive state in which the conversion can be initiated by the physical signal, and by means of at least one of the first and a second optical signal (b) into one of the first non-reactive state and a second non-reactive state. This method comprises forming a converting front of light comprising one of the first optical signal and a combination of the first and second optical signals in the conversion area, wherein the intensity of the light, over a depth of the converting front which is smaller than the diffraction limit at the wavelength of the light, increases so steeply that a portion of the substance in the reactive state over the depth of the converting front increases from essentially zero due to transferring the substance (a) out of the first non-reactive state into the reactive state, and decreases to essentially zero again due to transferring the substance (b) into the one of the first and second non-reactive states. This method further comprises moving the converting front over the conversion region in a direction opposite to the increase of the intensity of the light over the depth of the converting front; and applying the physical signal at least to a longitudinal part of the converting front, if the converting front is in selected positions in the conversion region.

The present invention further relates to a process of determining the distribution of a substance in a measurement region, the substance being selected from a group of substances which display at least one of the following transfer properties:
  the substance, by means of a first optical signal, is transferable (a) out of a first state in which no measurement signal is available from the substance into a measurement state in which a measurement signal is available from the substance,
  the substance, by means of at least one of the first optical signal and a second optical signal, is transferable (b) into one of the first state and a second state in which no measurement signal is available from the substance.

The process comprises forming a measuring front of light comprising one of the first optical signal and a combination of the first and second optical signals in the measurement region, wherein the intensity of the light, over a depth of the measuring front which is smaller than the diffraction limit at the wavelength of the light, increases so steeply that a portion of the substance in the measurement state over the depth of the converting front displays one of the following courses
  (i) an increase from essentially zero up to a saturation value due to transferring the substance (a) out of the first state into the measurement state,
  (ii) a decrease from a starting value to essentially zero due to transferring the substance (b) into the one of the first and second states in which no measurement signal is available from the substance,
  (iii) an increase from essentially zero due to transferring the substance (a) out of the first state into the measurement state and a decrease from back to essentially zero due to transferring the substance (b) into the one of the first and second states in which no measurement signal is available from the substance;

The process further comprises moving the measuring front over the measurement region in a direction opposite to the increase of the intensity of the light over the depth of the measuring front; at least recording the measurement signal emitted out of the measuring front for different positions of the measuring front in the measurement region; and assigning the recorded measurement signal to the corresponding position of the measuring front in the measurement region Other features and advantages of the present invention will become apparent to one with skill in the art upon examination of the following drawings and the detailed description. It is intended that all such additional features and advantages be included herein within the scope of the present invention, as defined by the claims.

SHORT DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

In this description, the term "distribution of the substance" does not only include the meaning of a distribution of the substance as such but also the meaning of a distribution of a certain permanent basic state of the substance, like for example a stable conformation basic state which is not altered during determining the distribution of the substance.

Further, in this description, the term "region" or "measurement region" or "conversion region" designates a region extending in one, two or three dimensions, i.e. along a line, over an area or over a volume, respectively. A region extending in one or two dimensions may be so small in the further second and third or the further third spatial direction(s) that (or there may be other reasons why) a resolution of the distribution of the substance in the further direction(s) is not possible or not of interest.

The step of transferring (b) into the one of the first and second state in which no measurement signal is available from the substance, or into the one of the first and second non-reactive state may start from the measurement or reactive state or from the first state.

The measurement state of the substance may be an electronic state of the substance which is an excited state of the substance as compared to its first state and out of which the substance spontaneously emits luminescence light, particularly fluorescence light. In this case, the first optical signal is excitation light which transfers the substance out of the energetically lower first state into the measurement state. Out of the electrically excited luminescent measurement state, the substance may—for example by the excitation light itself or by a second optical signal—be transferred into a dark state, like for example a triplet state, or by stimulation light returned into its one or any other energetically lower state out of which no spontaneous emission of fluorescence light is possible anymore. Particularly all common fluorescent dyes and all other luminescent substances belong to the group of substances displaying these properties.

The measurement state of the substance may, however, also be a conformation state or any other state of the substance out of which is can be excited by means of excitation light for the emission of luminescence light or for providing any other optical measurement signal, whereas the first state is a conformation state or any other state of the substance in which the respective measurement signal is not available at all or at least not available at a relevant level even after excitation of the substance. In this case, the second state of the substance may either be a further conformation state or a dark state mainly differing from the measuring state electronically. All so-called switchable fluorescence dyes, switchable fluorescent proteins and activatable luminescence particles particularly belong to the group of substances displaying these properties.

Correspondingly, the reactive state of the substance may be a conformation state or an electronic or chemical state of the substance out of which the substance is excitable by means of a physical signal for the desired conversion, whereas any non-reactive state of the substance may be a conformation state or an electronic or chemical state out of which this conversion is not possible or at least not possible at a relevant level, even if the physical signal is present. The conversion results in a permanent or at least temporarily stable, i.e. lasting other state of the substance which, however, may be reversible. This means that the substance may be returned into its reactive or non-reactive basic state.

When the portion of the substance in the measuring or reactive state is essentially zero, it is not existing at all in an ideal case. For the method according to the present invention, however, it is sufficient if the portion of the substance in the measuring or reactive state which is described as "essentially zero" is close to zero or at least small as compared to the maximum portion of the substance in the measuring or reactive signal within the measuring front.

When using traditional microscopy methods for determining the distribution of a substance or initiating the conversion of a substance, the achievable spatial resolution is affected by diffraction which occurs whenever light is focused. Thus in traditional microcopy, the resolution that can be obtained is given by the lower diffraction limit of about half of the wavelength of the light used.

Independently on the substance and the particular application, the present invention relates to getting beyond the wavelength-dependent diffraction limit of spatial resolution in determining the distribution of the substance or in initiating the conversion of the substance, i.e. to achieving a spatial resolution that is better than the diffraction limit.

In the first case (i) of the process of the present invention, the substance in front of the measuring front is not yet in the measuring state but in its first state out of which no measurement signal is available from the substance. Behind the measuring front, a portion of the substance is in the measuring state. This portion corresponds to a saturation value, i.e. to a value which could, at least not significantly, be increased by further increasing the intensity of the optical signal and which is not significantly increased by any present further increase of the intensity of the optical signal behind the measuring front.

In the second case (ii) of the process of the present invention, a certain portion of the substance in front of the measuring front is in the measuring state. Behind the measuring front the substance is no longer in the measuring state but in the first or second state out of which no measurement signal is available from the substance.

In the third case (iii) of the process of the present invention, the substance neither in front of nor behind the measuring front but only in the measuring front is in the measuring state. In all cases (i), (ii) and (iii), a portion of the substance in a certain state increases over the measuring front due to transferring the substance up to a saturation value. In the cases (ii) and (iii), this is the portion of the substance in the first or second state. If the saturation value remains below 100% and if the measurement signal from the substance behind the measuring front which is still in the measuring substance not so low that it may be neglected, it can easily be separated during evaluation of the recorded measurement signal as its intensity is determined by the respective saturation value or its complement. Besides the intensity of the respective optical signal, reaching the saturation threshold value depends on the effective cross-sections in exciting the transfers involved. These effective cross-sections will often be dependent on the environment of the substance. In any case, the respective transfer is driven up to its saturation if a calculable saturation intensity for the respective transfer in the measuring front is exceeded by the intensity of the respective optical signal by a factor of at least five or by one or more orders of magnitude.

In the process and method of determining the distribution of a substance in a measurement region according to the present invention, the measuring front is moved in a direction opposite to the increase of the intensity of the optical signal and/or the further optical signal over the measuring area to scan the measuring area with the measuring front. During scanning the measuring area with the measuring front, the measurement signal, at least out of the measuring front, or its variation is recorded and assigned to the respective positions of the measuring front in the measuring area. Preferably the distribution of the measurement signal or its variation is recorded with spatial resolution along the width of the measuring front extending perpendicular to the increase of the intensity of the first and/or second optical signals. This means that at least one distribution of the measurement signal or its variation is registered for each position of the measuring front in the measuring area. In case of a measuring area extending in one dimension only, it may however be sufficient, for example, to only record an intensity of the measurement signal or its variations in one or more individual width sections of the measuring front instead of a distribution of the measurement signal or its variation over the entire width of the measuring front.

In the process and method of determining the distribution of a substance in a measurement region according to the present invention, the spatial resolution in determining the distribution of the substance in the direction of moving the measuring front is particularly obtained by knowing the respective position of the measuring front in the sample, because the measurement signal, in the case (iii) of the process and in the method, may only origin out of the measuring front and because the measurement signal in the two other cases (i) and (ii) of the process may only display a non-predictable and thus separable variation due to the substance passing the measuring front. The spatial resolution along the measuring front may be achieved by analyzing the distribution of the measurement signal along the measuring front. In general, the spatial resolution of this distribution is limited by the diffraction limit (at the wavelength of the measurement signal). The measuring front, however, may be formed with a very small depths which may clearly surpass the diffraction limit so that the spatial resolution in the direction of the movement of the measuring front is increased far beyond the diffraction limit.

By means of orienting and moving the measuring front with regard to the measurement region in different directions, particularly by means of orienting a straight measuring front in directions orthogonal to or at least linearly independent of each other and by moving the measuring front perpendicular to its direction of main extension in both orientation, the distribution of the substance of interest in the measurement volume may be imaged in all directions at a spatial resolution beyond the diffraction limit even if the intensities of all optical signals forming the measuring front are constant along the measuring front or do not have a structure suitable for increasing the spatial resolution in this direction.

In the process and method of determining the distribution of a substance in a measurement region according to the present invention, at least all optical signals whose intensities strongly increase over the measuring front essentially have no intensity in front of the measuring front which would be sufficient for driving any changes of state of the substance. The measuring front in which the substance is measured for the first time thus approaches a point of the measurement region without causing a plurality of changes of state of the substance at this point already prior to reaching it with the measuring front. In an ideal case, the state of the substance is changed for the first time when the substance is reached by the measuring front.

For forming the measuring front, the respective first and second optical signal(s) may be perpendicularly focused to the desired line of the measuring front. Generally, the boundary of the focus volume of one or more optical signals focused to a point may also be used as the measuring front. I.e. the measuring front needs not to have a straight run; preferably, however, it is straight. For forming a straight measuring front, a cylinder lens may be used, for example, which focuses a bundle of parallel beams of light expanded in one direction to a straight line. The distribution of the intensity of the optical signal focused in this way comprises dimensions in lateral direction which may not get beyond the diffraction limit, i.e. they may not be smaller than the diffraction limit. With a high intensity of the optical signal, however, the boundary of the distribution of the intensity of the signal comprises such a steepness that an increase of the intensity which is needed for forming a measuring front according to the present invention occurs over a small distance or depth of the measuring front which is far below the diffraction limit. The very high intensities of the optical signal(s) in a maximum of intensity distribution adjacent to the measuring front are essentially harmless as the substance in the measurement value is subjected to these intensities and to the resulting plurality of changes of state only after it has been crossed by the measuring front and measured therein.

A further proactical option to particularly form a straight measuring front is the projection of an edge into the measurement region. Here, side maxima of the intensity distribution of the optical signal(s) in front of the measuring front are harmless, as a rule, as they are either only weak and/or sufficiently far away from the steep increase of intensity over the edge to discriminate their effects on the measurement signal easily. The image of an edge along which the measurement region is divided in two partial volumes is a preferred embodiment of the formation of the measuring front in the cases (i) and (ii) of the process of the present invention.

If a further optical signal besides the optical signal is needed for the two transfers of the substance (a) out of the one state into the measurement state and (b) into the one or the further state, these two signals may be shaped together for forming the measuring front. They may also have a slight offset perpendicular to the run of the measuring front, i.e. in the direction of the depth of the measuring front, if, for example, no full overlap of the two optical signals is suitable.

In the process and method of determining the distribution of a substance in a measurement region according to the present invention, besides the fact that the depth of the measuring front out of which the measurement signal may origin, a relative intensity distribution of the measurement signal from the substance may also be used for spatially resolving the position of the molecules of the substance in the measurement region. The relative intensity distribution of the measurement signal from the substance depends on the position of the molecules of the substance in depth direction of the measuring front and typically continuously increasing with the intensity of the optical signal over the depth of the measuring front until it drops abruptly. This is a spatial effect of a second order which may be used for enhancing the spatial resolution. An increase of the spatial resolution of a first order is achieved in the process and method of determining the distribution of a substance in a measurement region according to the present invention in that the measurement signal or the variation of the measurement signal from the substance only occurs over the depth of the measuring front, i.e. when the substance is in or passes the depth of the measuring front.

If the substance by means of one optical signal is both transferable (a) out of the first state in which no measurement signal is available from the substance into the measurement state and (b) into the second state, it is sufficient for forming a measuring front having a depth below the diffraction limit, wherein the measurement signal is only available from the substance in the area of the measuring front, that the intensity of the one optical signal increases over the depth of the measuring front which is smaller than the diffraction limit at the wavelength of the optical signal in such a way that the portion of the substance in the measurement state at first increases by transferring the substance (a) out of the first state into the measurement state and then drops again towards zero due to the transfer of the substance (b) into the second state becoming predominant.

In actual embodiments of this variant of the process of the present invention, the substance is a luminescence dye, particularly a fluorescence dye, the measurement state being an excited electronic state out of which the substance spontaneously emits luminescence light, i.e. particularly fluorescence light, as the measurement signal, and the second state being a dark state having a lifetime which is longer than a measurement duration over which the measurement signal is recorded from the same position of the measuring front in the sample. This means that the substance returns out of its dark state into its basic state out of which it may excited for luminescence again, but only then when it is no longer in the area of the measurement region out of which the measurement signal is recorded and assigned to the present position of the measuring front in the sample. Such dark states are typical for nearly all common fluorescence dyes and many other luminescence dyes. Often, these dark states are triplet states, whereas the measurement state is an excited singlet state. The dark state may also be an ionized state. Fluorescence and other luminescence dyes, as a rule, return out of such dark states at least a few times before they are finally, i.e. photo-chemically bleached. In the process and method of determining the distribution of a substance in a measurement region according to the present invention, only very few movements of the measuring front over the sample out of different directions, mostly only two movements in two orthogonal directions are necessary to image the structure of interest in the sample completely at a high spatial resolution. Thus, the substance only needs to return once or very few times out of its dark state into its basic state.

The latter variant of the process according to the present invention requires a certain selection of the substance whose distribution in the measurement region is determined. Even if such a substance is available, the execution of this variant of the method according to the present invention may be complex. Thus, other variants of the process and method of determining the distribution of a substance in a measurement region according to the present invention may be preferred in which the light whose intensity increases over the depth of the measuring front comprises two optical signals of different wavelengths whose intensity distributions in the measurement region are structured in the same way, wherein the substance by means of the first optical signal is transferred (a) out of the first state in which no measurement signal is available from the substance into the measurement state, and by means of the second optical signal (b) into the first or second state in which no measurement signal is available from the substance.

In these variants of the process and method of determining the distribution of a substance in a measurement region according to the present invention, two optical signals of different wavelengths are used in the measuring front to be able to use a higher bandwidth of substances for providing the measurement signal. However, the optical signals are formed or structured in the same way, i.e. with the same optical elements, for forming the measuring front. Thus, they generally have the same intensity distribution over the measuring front even if their absolute intensity may differ. The overall complexity of the method or process is thus not relevantly increased by the at least one further optical signal of another wavelength. Particularly, no different optical elements for differently structuring a plurality of optical signals have to be aligned with regard to each other as in common STED or RESOLFT methods. Instead, it is sufficient to superimpose the optical signals without structure and to then structure them together.

Actually, in these variants of the process and method of determining the distribution of a substance in a measurement region according to the present invention in which the measuring front is formed of at least two optical signals of different wavelengths, the substance may emit fluorescence light in the measurement state and no fluorescence light in the first or second state, because the measurement state is an excited state of the substance out of which it spontaneously emits fluorescence light whereas the first or second state is a not excited state or at least a state of the substance out of which no emission of fluorescence light takes place. In this case, the first optical signal which transfers the substance into the measurement state may be excitation light, whereas the second optical signal may, for example, be so-called STED or GSD light. Alternatively, the substance may only be excitable for emission of fluorescence light by means of excitation light out of the measurement state, and it may not be excitable for the emission of fluorescence light with the excitation light in the first or second state. Also in this case, the fluorescence light is the measurement signal, but the excitation light has to be applied in addition to the two optical signals forming the measuring front. The additional excitation light may also have an intensity increasing over the measuring front and it may be structured in the same way or with the same optical elements as the two other optical signals. It may, however, also be homogenously applied over the entire measurement region, for example. It is also possible that the excitation light has the same wavelength as the first and second optical signals which are already present in the measuring front. Then, no further excitation light is needed but the respective optical signal, besides the function of transferring the substance into the measurement state or into the first or second state in which no measurement signal is available from the substance, also fulfills the task of exciting the substance in the measurement state for the emission of fluorescence light.

If the substance, behind the area of influence of the optical signal(s) effecting its transfer(s), very quickly returns into its basic state in which it is present in front of the measuring front, or if the substance is anyhow returned into this basic state by the optical signal, the measurement region may, for example, be scanned with several parallel or inclined measuring fronts in a quick sequence. If the substance needs a longer recovery time before it returns in its starting state, it may be waited for this recovery time prior to scanning the measurement region with the measuring front again, or an incomplete recovery of the substance may be considered when evaluating the measurement signal recorded during scanning the substance with the measuring front again. Often it is advantageous if the substance in the measurement region over which the measuring front has already been moved is subjected to a resetting or refreshing optical signal, particularly of the blue or ultraviolet range of wavelengths, before the measuring front is once again moved over the measurement region. In this way, the portion of the substance in the basic state which it had prior to scanning the measurement are with the measuring front for the first time may often be increased considerably.

It has to be underlined that the present invention may not only be executed using fluorescence dyes and other luminescence dyes. Instead, it is sufficient that the substance provides any light emitting or scattering centers which may be transferred into or out of a measurement state according to the present invention, wherein the measurement signal from the substance is only available in its measurement state. This does not necessarily mean that no measurement signal at all may be obtained from the sample in other states of the substance, as long as it does not have the same intensity and/or it is not the same measurement signal as that one which is obtained from the substance within the measurement according to the present invention.

In the method of the present invention, so-called switchable fluorescence dyes, switchable fluorescent proteins and activatable luminescence particles which may be switched out of one conformation state into another conformation state by means of a switching signal may also be used. Here, the two conformation states may be the first state. I.e. the starting or basic state of the substance in front of the measuring front, and the measurement state of the substance in the measuring front in which the substance is excitable for emission of luminescence or fluorescence light. Alternatively, the two conformation states may also be the first state, i.e. the starting or basic state of the substance in front of the measuring front, wherein the measurement state is an electronically excited state of this conformation state, and the second state, i.e. a dark state of the substance behind the measuring front. In these two cases, the measuring front is formed by a steep intensity distribution of the switching signal. Switchable substances may, however, also be used in that a relative basic concentration of the substance in a basic state excitable for luminescence is adjusted in the sample. For this purpose, the switching on signal of a comparatively low intensity may be applied in front of the measuring front or superimposed with the measuring front and at least not primarily involved in forming the measuring front.

In the process and method of determining the distribution of a substance in a measurement region according to the present invention, the measuring front may have a straight run in width direction. This is preferred but not essential. Thus, the measuring front may also be a part of a periphery of any other intensity distribution than one with a maximum intensity along a straight line.

Preferably, the measuring front has an extension in width direction of a high multitude of the diffraction limit at the wavelength of the optical signal and/or the further optical signal. Ideally, the measuring front spans the entire width of the measurement region.

The measuring front may be moved over the measurement region stepwise or continuously, wherein the transition from a stepwise to a continuous movement is smooth. Particularly, a continuous advance of the measuring front formed of pulsed optical signals directly corresponds to a stepwise advance of the measuring front.

In one embodiment, the measurement signal out of the measuring front, even if the measuring front is moved continuously, is recorded at temporal resolution. This may particularly mean that a plurality of distributions of the measurement signal out of the measuring front temporarily following each other are recorded for each position of the measuring front in the measurement region, even if the measuring front is moved continuously. From a temporal variation of these distributions of the measurement signal for one position of the measuring front conclusions can be drawn with regard to the relative position of the molecules of the substance providing the measurement signal within the measuring front. This allows for realizing a further increase of the spatial resolution at which the distribution of the substance in the sample is imaged according to the method of the present invention. Particularly, however, the signal-to-noise ratio of the measurement signal typically varies with time and may be optimized by adjusting the point in time at which the distribution of the measurement signal is recorded. This does, however, not necessarily require to record several distributions of the measurement signal out of the measuring front for each position of the measuring front in the measurement region. Instead, it is sufficient to optimize the time window in which a single distribution of the measurement signal is recorded after moving the measuring front in a new position. This technique is known as gating the measurement signal. The optimum gate may also be set according to an automated process in which the signal-to-noise ratio is optimized.

The distribution of the measurement signal out of the area of the measuring front may actually be recorded with a line detector aligned in width direction of the measuring front. A two-dimensional detector is not needed in the case (iii) of the process and in the method of determining the distribution of a substance in a measurement region according to the present invention, even if the presence of at least two measuring lines of a detector staggered perpendicularly to the measuring front may provide for additional advantages. The use of a line detector instead of a two-dimensional detector allows for very quickly reading out the individual pixels of the detector which is advantageous with regard to the desired temporal resolution of the distribution of the intensity of the measurement signal along the measuring front.

The line detector may have at least one measuring line parallelly offset with regard to the measuring front. Thus, its generally diffraction limited field of view may, for example, be arranged relative to the measuring front in the measurement region in such a way that it is mainly behind the measuring front where the substance in the measurement region does not provide any measurement signal anymore. This is of particular advantage if the substance is crossed by a side maximum of the intensity distribution of the optical signal in front of the measuring front. In any case, the position of the line detector is suitably not fixed but adjustable relative to any optics forming the measuring front, because, for example, the position of the measuring front with regard to these optics varies with the absolute intensity of the optical signals. The optimum adjustment of the relative position of the line detector may also be set in an automated process in which, for example, the signal-to-noise ratio is optimized.

A slot diaphragm in front of the line detector may be used to record the distribution of the measurement signal out of the measuring front confocally with regard to the measuring front. Here, confocally refers to all directions perpendicular to the measuring front. In this way, the spatial resolution of the process and method according to the present invention in z-direction, i.e. in direction of the optical axis of the measurement signal, may be enhanced. The line detector itself or small dimensions of the pixels of the line detector may also be used for confocally recording the measurement signal out of the measurement region. The slot diaphragm may then still be used for suppressing scattered light.

For enhancing the spatial resolution in z-direction, other generally known techniques are also applicable in the process and method according to the present invention, like for example multi photon excitation of a fluorescence dye, registering the measurement signal by means of several objectives, such as in 4Pi fluorescence light microscopy, and so on.

A multi photon excitation of one or both changes of state desired in the area of the measuring front also has the advantage of increasing the effective steepness of the transfer probability in the direction of the depth of the measuring front and thus of a reduction of the effective depth of the measuring front.

If the measurement signal from the substance in the measuring front as recorded with the detector can be assigned to individual molecules of the substance, the position of the molecules in the sample, particularly in the direction along the measuring front, may also be determined based on the distribution of the measurement signal over neighboring pixels of the detector at a high spatial resolution surpassing the diffraction limit. The narrow depth of the measuring front may allow for assigning the recorded measurement signal to individual molecules of the substance even at comparatively high absolute concentrations of the substance. If such an assignment of the measurement signal to individual molecules of the substance is possible, it is sufficient to scan the measurement region with the measuring front only once, i.e. only in one direction. The position of the individual molecules of the substance in the sample will then typically be determined from the position of the measuring front in its advancing direction and from the distribution of the measurement signal over the detector in the direction along the measuring front.

In the cases (i) and (ii) of the process according to the present invention, however, a two-dimensional detector array covering the entire measurement region is preferably used to record the variation of the measurement signal with the advance of the measuring front over the measurement region at a spatial resolution perpendicular to the measuring front, i.e. in the direction of the depth of the measuring front. In case (i) the advancing measuring front, in the area presently scanned by the measuring front, successively transfers further portions of the substance into the measurement state so that the measuring front subdivides the measurement region in a partial volume in which the substance is in the measurement state and into a partial volume in which the substance is not yet in the measurement state. Case (ii) essentially only differs from case (i) in that the positions of the two partial volumes are reversed with regard to the direction of movement of the measuring front. In both cases (i) and (ii), not the measurement signal directly recorded by the detector array but the variation of this measurement signal with the advance of the measuring front is relevant. Generally, a two-dimensional detector may also be used in case (iii) of the process and in the method of the present invention.

It is to be understood that the depth of the measuring front in the process and method of the present invention only extends over a small fraction of the diffraction limit at the wavelength of the first and second optical signal. Its extension in this direction may be reduced to ¹⁄₁₆ of the diffraction limit or less. With the depth of the measuring front getting smaller, the spatial resolution of the image of the structure of interest obtained according to the process and method of the present invention gets better.

As the first and second optical signals are only applied to the substance very few times with in the process and method of the present invention, very sensitive substances may be used, on the one hand, and the first and second optical signals may have a comparatively high energy, i.e. the wavelengths of the first and second optical signals which linearly influence the absolute height of the diffraction limit may be comparatively short, on the other hand. Thus, these wavelengths may, for example, be shorter than 450 nm or even not be longer than 400 nm, and particularly they may be in a range of 350-400 nm, i.e. at the lower end of the visible light. Light of such wavelengths is available from powerful pulsed and cw lasers. Besides these optical signals of the UV range, the method according to the present invention, however, may also be applied with optical signals of the entire visible range up to the infrared range.

Both pulsed and cw lasers may be used as light sources for the first and second optical signals in the process and method according to the present invention. This means, all optical signals may be applied in form of pulses or at a temporarily constant intensity in the process and method of the present invention. In case of pulses, however, they should have a very quick consecution as compared to the velocity of moving the measuring front to scan the measurement region without gaps.

The process and method according to the present invention of determining the distribution of the substance in the measurement region may not only be used for imaging a structure in a sample marked with the substance but also for reading information from a data carrier which is coded by the distribution of the substance. Here, the substance may particularly be arranged in several tracks at distances of at least the diffraction limit at the wavelength of the measurement signal. The measuring front may be oriented perpendicular to the tracks when reading the information.

The scanning light microscope according to the present invention comprises an optic for forming a measuring front of the first and second optical signals coming from a light source. Further, a detector for recording the distribution of the measurement signal coming from the sample out of the measuring front is provided. This detector preferably is a line detector.

In the method of initiating a conversion of a substance in a conversion area at high spatial resolution according to the present invention, a conversion front of the first and second optical signals is formed in the conversion area, wherein the intensities of the first and second optical signals increase over a depth of the conversion front which is smaller than the diffraction limit at the wavelengths of the first and second optical signals from no transfer of the substance out of a first non-reactive state into the reactive state up to a complete transfer out of the reactive state into the first or a second non-reactive state. This conversion front is moved in opposite direction to the increase of the intensities of the first and second optical signals over the conversion area; and the physical signal for initiating the conversion of the substance being in the reactive state is applied to at least a partial area of the conversion front when the conversion front is in selected positions within the conversion area.

The physical signal is preferably applied at a spatial resolution along the conversion front running perpendicular to the increase of the intensities of the first and second optical signals.

The method of initiating a conversion of a substance in a conversion area at high spatial resolution according to the present invention may, for example, be applied in microlithography and/or for locally releasing effector molecules. It may also be used for storing information, wherein the conversion may be reversible or non-reversible. For storing information, the substance may be arranged in one or more tracks which are arranged at a distance of at least the diffraction limit at the wavelength of the physical signal, wherein the conversion front is oriented perpendicular to the tracks and wherein the physical signal is applied with spatial resolution between the tracks. Actually, for example, 8 tracks may be arranged side by side to be able to store one byte of information at each position of the conversion front. In one or more additional tracks, synchronization signals may be written for rereading the information.

Besides the particularities described here, the method of locally initiating a conversion of a substance in a conversion area according to the present invention may correspond to the disclosure of DE 103 25 459 A1 and the members of the respective patent family and of those documents which have been cited in the examination procedures of the members of this patent family and to any published further development based on one of these documents.

The reactive states of the substances usable in the method of locally initiating a conversion of a substance in a conversion area according to the present invention, besides conformation states, also include electronic and chemical states, wherein—in the entire present description—the term "electronic state" should be interpreted so broad that it also includes an ionized state.

Figure 1:
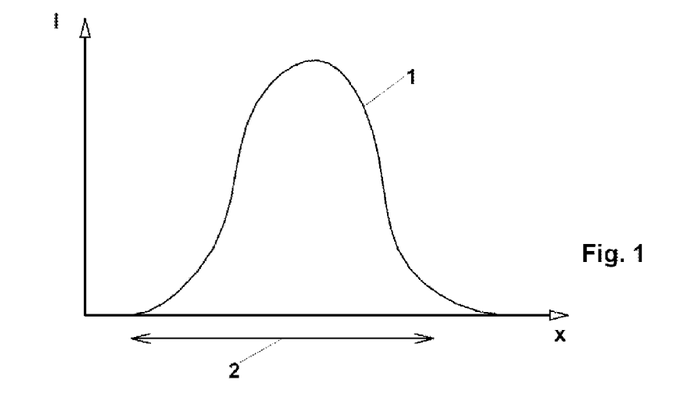
FIG. 1 shows a diffraction-limited intensity profile of an optical signal.

Referring now in greater detail to the drawings, FIG. 1 is an intensity profile of a diffraction-limited optical signal 1. The intensity distribution is Gauss-shaped and extends over an area 2 whose minimum dimensions are limited by Abbe's diffraction limit which is about half the wavelength of the optical signal 1.

Figure 2:
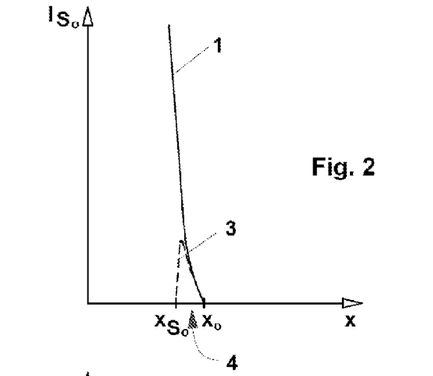
FIG. 2 shows a border area of the intensity profile according to FIG. 1 at a very high absolute intensity of the optical signal and an intensity distribution of a measurement signal resulting from this intensity distribution of the optical signal.

FIG. 2 illustrates a case in which the intensity of the optical signal 1 is very high. Thus, it already increases very quickly in the periphery of the intensity distribution according to FIG. 1 which is depicted in FIG. 2 at an enlarged scale. Thus, if the optical signal 1 is excitation light for the excitation of a fluorescence dye for spontaneous emission of fluorescence light, for example, very quickly after exceeding the intensity of 0 at $x_0$, an intensity $S_D$ is exceeded at $x_{SD}$ at which already a saturation of a temporary transfer of the fluorescence dye into a dark state is reached. This means that only in the area between $x_0$ and $x_{SD}$ a measurement signal 3, i.e. fluorescence light in the present example, is emitted by the fluorescence dye. This area between $x_0$ and $x_{SD}$ is designated as measuring front 4 here. The depth of the measuring front 4 in the direction of the intensity profile between $x_0$ and $x_{SD}$, due to the very high intensity of the optical signal 1, is depending on time.

Directly after applying the optical signal 1, the depth of the measuring front may larger as the fluorescence dye even in areas of higher intensity of the optical signal 1 is not instantaneously transferred into its dark state but emits fluorescence light first. With time, the depth of the measuring front becomes narrower. Further, the intensity of the measurement signal 3 decreases. Thus, the measurement signal 3 is ideally recorded at a temporal resolution after applying the optical signal 1 and then analyzed for the point in time at which the measurement signal displays the optimum signal-to-noise ration, on the one hand, and a high spatial limitation over a narrow depth of the measuring front 4, on the other hand.

Figure 3:
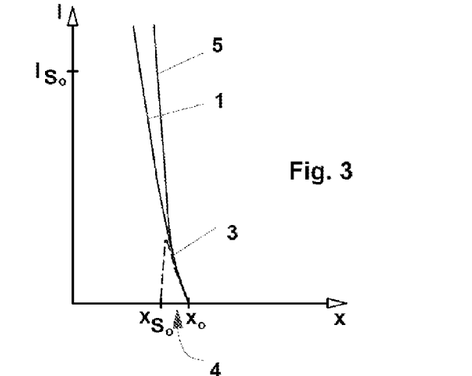
FIG. 3 is a diagram corresponding to FIG. 2 for a case in which the measurement signal, besides the optical signal, depends on a further optical signal that also has a diffraction-limited intensity distribution.

FIG. 3 illustrates a case in which not only one optical signal 1 but also a further optical signal 5 is applied which, in principle, has the same intensity distribution as the optical signal 1 but an even higher absolute intensity. Actually, the further optical signal 5 may be one which purposefully transfers the fluorescence dye into a dark state whereas the optical signal 1 essentially only serves for exciting the fluorescence dye for fluorescence. In this case, the onset of the optical signal 1 determines the first point $x_0$ of the measuring front 4, whereas the saturation intensity $S_D$ of the optical signal 5 at which the fluorescence dye is essentially completely transferred into the dark state defines the last point $x_{SD}$ of the measuring front 4. With regard to the temporal dynamic of the width of the measuring front 4, the same applies what has already been remarked on FIG. 2.

Figure 4:
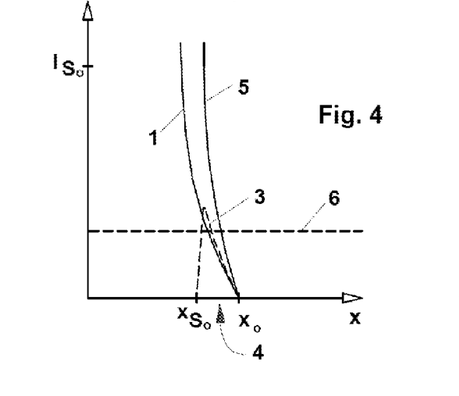
FIG. 4 is a diagram corresponding to FIG. 2 for a case in which the measurement signal, besides the optical signal and the further optical signal with diffraction-limited intensity distribution, is generated by means of even a further optical signal with a homogenous intensity distribution.

FIG. 4 illustrates a case in which the optical signal 1 switches a switchable fluorescence dye on, i.e. into a state excitable for fluorescence, whereas the further optical signal 5 switches the fluorescence dye off, i.e. into its original or another state not excitable for fluorescence. In addition to the optical signals 1 and 5, an even further optical signal 6 in form of excitation light having a homogenous intensity distribution is applied here, which excites the fluorescence dye being in the switched on state for fluorescence. Also here, the distribution of the measurement signal 3 is limited to the measuring front 4 which has one dimension much smaller than the diffraction limit. Often, with switchable fluorescence dyes, the further optical signal 5 may both be used for exciting the switched-on fluorescence dye for fluorescence and for switching the fluorescence dye off, i.e. back into its original state so that there is no need for separate excitation light in form of the even further optical signal 6.

FIG. 4 may also be used for explaining a case in which the optical signals 1 and 5 generally have the same function as in FIG. 3, i.e. the optical signal 1 excites a fluorescence dye for fluorescence, and the optical signal 5 switches the fluorescence dye into a dark state. In this case, the optical signal 6 with homogenous intensity distribution, however, is no excitation light but a switch-on signal which transfers a certain portion of a fluorescence dye which is present at a higher absolute concentration out of a state not excitable for fluorescence by the optical signal 1 into a state excitable for fluorescence by the optical signal 1. Also in this case, a distribution of the measurement signal 3 results which only extends over the measuring front 4 having a depth essentially reduced below the diffraction limit.

Figure 5:
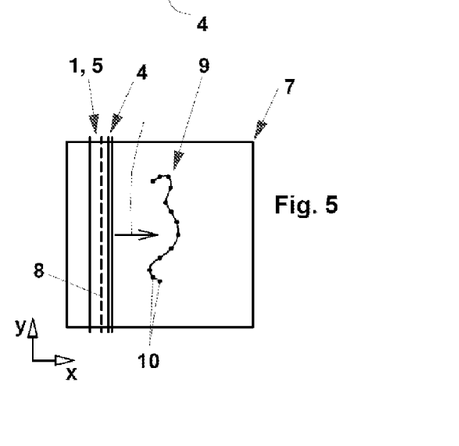
FIGS. 5 and 6 illustrate scanning a sample and a structure of interest included therein with a measuring front comprising the intensity distributions according to any of the FIGS. 1 to 4 in two orthogonal directions.
Figure 6:
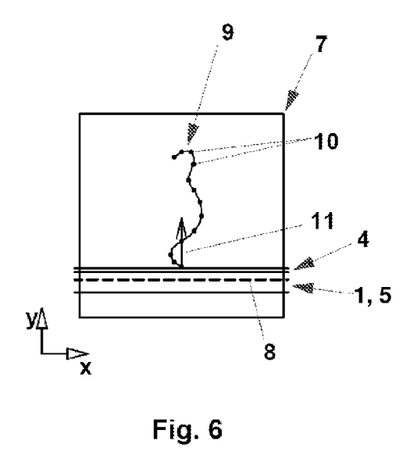

FIGS. 5 and 6 illustrate scanning a sample 7 as an example of a measurement region in two different directions x and y with a straight measuring front 4. Further, the entire intensity distribution of the optical signals 1 and 5 according to FIG. 3 which are used here is depicted. A dashed line 8 indicates the maximum of this intensity distribution. A structure of interest 9 included in the sample 7 which is marked with a substance 10 in the form of molecules of a fluorescence dye is imaged by registering the fluorescence light from the fluorescence dye as the measurement signal. Here, registering the measurement signal is executed with spatial resolution along the measuring front 4. The spatial resolution in this registration is principally limited by diffraction as long as the measurement signal is not registered for individual molecules of the substance 10 over several pixels and evaluated with regard to the center point of this intensity distribution. This statistical method may also applied in the process and method according to the present invention. Then, however, it will typically only be applied in the direction along the measuring front 4. In the direction perpendicular to the measuring front 4 in which the measuring front 4 is moved over the sample 7 and which is indicated by arrows 11 here, the assignment of the measurement signal to a particular location in the sample is made via the position of the measuring front in the sample. As the dimension of the measuring front 4 in this direction is far below the diffraction limit, the spatial resolution in imaging in this direction is much better than the diffraction limit. In that the sample, as depicted in FIGS. 5 and 6, is scanned in two orthogonal directions x and y with the measuring front 4, the structure 9 of interest can be imaged in both directions with the spatial resolution surpassing the diffraction limit perpendicular to the measuring front 4.

Figure 7:
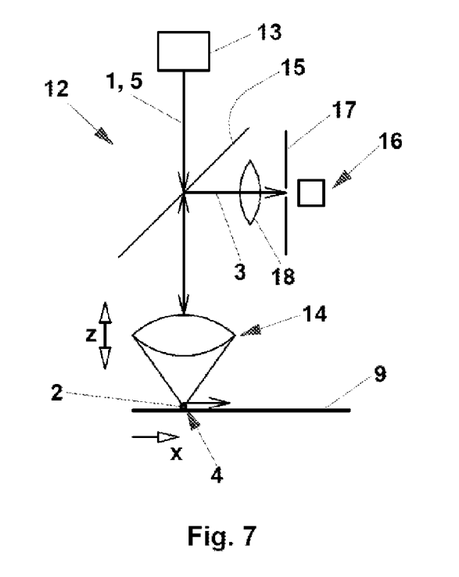
FIGS. 7 and 8 illustrate a light scanning microscope for scanning the sample with the measuring front according to FIGS. 5 and 6 and for simultaneously recording the measurement signal out of the measuring front.
Figure 8:
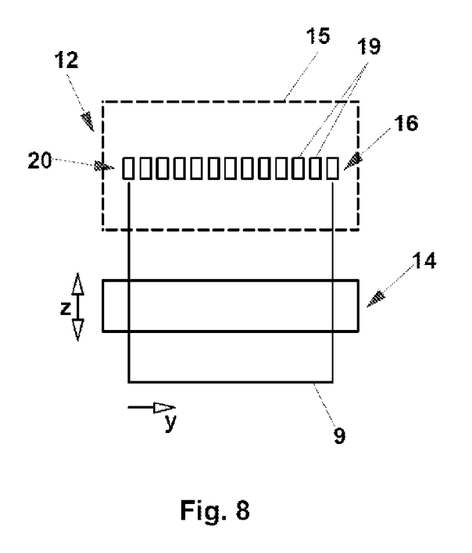

The fluorescence light microscope 12 illustrated in FIGS. 7 and 8 for measuring the sample 9 according to FIGS. 5 and 6 comprises a light source 13 which provides the optical signals 1 and 5 together in form of a bundle of beams with a nearly line-shaped cross-section. This bundle of beams is focused by an objective 14 orthogonal to the direction of main extension of its cross-section into the area 2 in which the intensity distributions of the optical signals 1 and 5 according to FIG. 3 result. The measurement signal 3 coming from the sample 9 in opposite direction is deflected by means of a dichroitic mirror 15 towards a line detector 16. In front of the line detector 16 a slot diaphragm 17 (only shown in FIG. 7) may be arranged to enhance the assignment of the measurement signal to a certain position in z-direction and to thus increase the spatial resolution of the structure of interest in z-direction. An optic 18 focuses the measurement signal 3 in the direction perpendicular to the run of the measuring front onto the slot diaphragm 17 or directly onto the line detector 16. The line detector 16 comprises at least one measuring line of pixels 19 arranged in a row. It is to be understood that the depiction in FIG. 8 is not to scale as a much higher number of pixels 19 are provided in a much denser arrangement within the measuring line 20. The line detector 16 may be read out at a high frequency and thus allows for resolving the temporal dynamic with regard to the depth of the measuring front 4 already mentioned when describing FIG. 2. The scanning velocity of the measuring front 4 across the sample 9 is also a parameter which may be varied to optimize the signal-to-noise ratio and the spatial resolution in imaging the structure 9.

Figure 9:
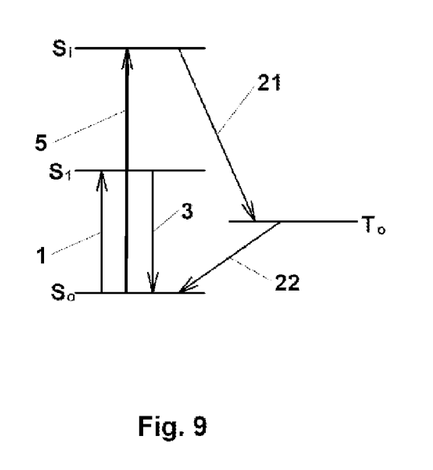
FIG. 9 illustrates the electronic states of a fluorescence dye used in the method of determining the distribution of the fluorescence dye according to the present invention.

FIG. 9 schematically illustrates, i.e. without depicting any sub-states, the electronic states of a fluorescence dye which may be used as the substance in the process and method according to the present invention of determining the distribution of the substance in a measurement region, if the substance, by means of the optical signal 1, is transferable (a) out of a first state in which no measurement signal is available from the substance into a measurement state, and by means of the optical signal 5 (b) into a second state in which no measurement signal is available from the substance anymore. The first state of the substance is the singlet ground state $S_0$ out of which an excitation into an excited electronic singlet state $S_1$ as a measurement state is possible by means of the optical signal 1. Out of the measurement state $S_1$ the fluorescence dye emits fluorescence light as the measurement signal 3. By means of the optical signal 5, however, the fluorescence dye is further excited in an energetically higher electronic second state. This can, as indicated here, be a singlet state $S_i$ but also an excited triplet state $T_i$. From there, the fluorescence dye gets into a dark state by means of a transition 21. This dark state is the long lasting triplet ground state $T_0$ which only slowly decays via a transition 22 back into the singlet ground state $S_0$. With increasing intensity of the optical signal 5 the probability strongly increases that the fluorescence dye gets into the dark state $T_0$ and remains there for such a long time so that no fluorescence light as the measurement signal may be emitted anymore until the measuring front is already far away from the considered fluorescence dye molecule. Alternatively, the fluorescence dye may be transferred with the optical signal 5 out of the excited electronic singlet state $S_1$ without fluorescence back into its ground state $S_0$ or into another dark state to avoid the emission of fluorescence light by means of an intensity of the optical signal 5 increasing beyond the saturation value for this transition.

Figure 10:
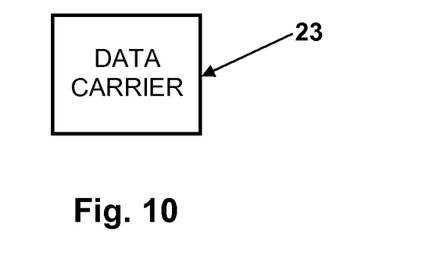
FIG. 10 schematically shows a data carrier.
Figure 11:
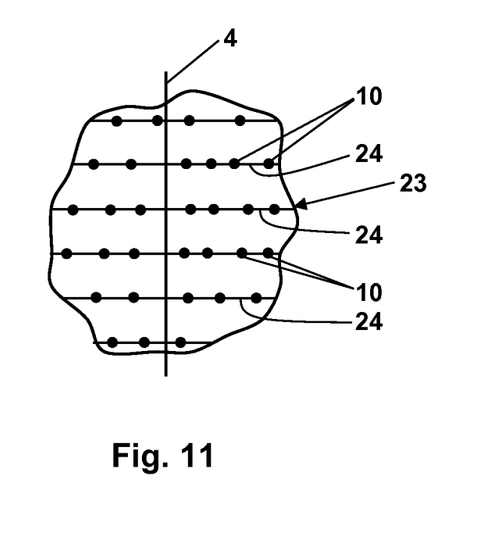
FIG. 11 shows a detail of the data carrier according to FIG. 10.

FIG. 11 shows a detail of the data carrier 23 schematically depicted in FIG. 10. In the detail according to FIG. 11, the substance 10 is arranged along tracks 24. The tracks are arranged at distances of at least the diffraction limit of the wavelength of the measurement signal. In reading information from the data carrier 23, the measuring front 14 is oriented perpendicular to the tracks.

Many variations and modifications may be made to the preferred embodiments of the invention without departing substantially from the spirit and principles of the invention. All such modifications and variations are intended to be included herein within the scope of the present invention, as defined by the following claims.

I claim:

1. A method of determining the distribution of a substance in a measurement region, the substance being transferable
    by means of a first optical signal (a) out of a first state in which no measurement signal is available from the substance into a measurement state in which a measurement signal is available from the substance, and
    by means of a second optical signal (b) into one of the first state and a second state in which no measurement signal is available from the substance, the method comprising:
    forming a measuring front of the first and second optical signals in the measurement region, wherein intensities of the first and second optical signals, over a depth of the measuring front in the direction of the combined intensity profiles of the first and second optical signals, the depth being smaller than the diffraction limit at the wavelengths of the first and second optical signals, increase so steeply that a portion of the substance in the measurement state over the depth of the measuring front increases from essentially zero due to transferring the substance by means of the first optical signal (a) out of the first state into the measurement state, and decreases to essentially zero again due to transferring the substance by means of the second optical signal (b) into the one of the first and second states;
    moving the measuring front over the measurement region in a direction opposite to the increase of the intensities of the first and second optical signals over the depth of the measuring front;
    at least recording the measurement signal emitted out of the measuring front for different positions of the measuring front in the measurement region; and
    assigning the recorded measurement signal to the corresponding position of the measuring front in the measurement region,
    wherein the first and second optical signals have different wavelengths, wherein the intensity distributions of both the first and second optical signals over the measuring front are structured by the same optical elements, and wherein the first and second optical signals whose intensities increase over the measuring front essentially have no intensity in front of the measuring front being sufficient for driving any changes of state of the substance.

2. The method of claim 1, wherein a distribution of the measurement signal is recorded with spatial resolution along the measuring front and assigned to the corresponding position of the measuring front in the measurement region.

3. The method of claim 1, wherein the measuring front is straight, and wherein the intensities of the first and second optical signals increasing over the depth of the measuring front are constant along the measuring front.

4. The method of claim 3, wherein the measuring front is moved in two linearly independent directions over the measurement region.

5. The method of claim 1, wherein the measuring front spans over at least hundred times an diffraction limit at the wavelengths of the first and second optical signals.

6. The method of claim 1, wherein the measuring front extends over a full width of the measurement region.

7. The method of claim 1, wherein the measurement signal is recorded with temporal resolution for each position of the measuring front in the measurement region.

8. The method of claim 2, wherein the distribution of the measurement signal is recorded with a line detector aligned along the measuring front.

9. The method of claim 1, wherein a distribution of the measurement signal is recorded with a detector array covering the entire measurement region.

10. The method of claim 1, wherein the intensities of the first and second optical signals increase so steeply over the measuring front that the depth of the measuring front over which the portion of the substance in the measurement state increases from essentially zero, and decreases to essentially zero again is smaller than half of the diffraction limit at the wavelengths of the first and second optical signals.

11. The method of claim 1, wherein the substance emits fluorescence light in the measurement state and no fluorescence light in the one of the first and second states.

12. The method of claim 1, wherein the substance is excitable for emission of fluorescence light by means of excitation light in the measurement state and not excitable for the emission of the fluorescence light by means of the excitation light in the one of the first and second states, the fluorescence light being the measurement signal.

13. The method of claim 1, wherein a resetting optical signal is applied to the substance in the measurement region over which the measuring front has been moved prior to moving the measuring front again over the measurement region.

14. The method of claim 13, wherein the resetting optical signal is selected from the blue to ultraviolet wavelength range.

15. The method of claim 1, wherein the measurement region is a part of a data carrier and wherein the distribution of the substance in the measurement region is transcribed into data stored on the data carrier.

16. The method of claim 15, wherein the substance is arranged in tracks arranged at a distance of at least the diffraction limit at the wavelength of the measurement signal and wherein the measuring front is aligned perpendicular to the tracks.

17. A scanning light microscope for determining the distribution of a substance in a measurement region, comprising
a light source configured to provide first and second optical signals of different wavelength, wherein the first optical signal transfers the substance out of a first state in which no measurement signal is available from the substance into a measurement state in which a measurement signal is available from the substance, and the second optical signal transfers the substance into one of the first state and a second state in which no measurement signal is available from the substance
optics configured to form a measuring front of the first and second optical signals in the measurement region, wherein intensities of the first and second optical signals, over a depth of the measuring front in the direction of the combined intensity profiles of the first and second optical signals, the depth being smaller than the diffraction limit at the wavelengths of the first and second optical signals, increase so steeply that a portion of the substance in the measurement state over the depth of the measuring front, increases from essentially zero due to transferring the substance by means of the first optical signal (a) out of the first state into the measurement state, and decreases to essentially zero again due to transferring the substance by means of the second optical signal (b) into the one of the first and second states
a scanner configured to move the measuring front with regard to the measurement region, and
a detector configured to at least record a distribution of the measurement signal emitted out of the measuring front with spatial resolution along the measuring front,
wherein the optics comprise same optical elements for structuring intensity distributions of the first and second optical signals over the measuring front, wherein the first and second optical signals whose intensities increase over the measuring front essentially have no intensity in front of the measuring front being sufficient for driving any changes of state of the substance.

18. The scanning light microscope of claim 17, wherein the detector includes a line detector.

19. A method of locally initiating a conversion of a substance in a conversion region, the substance being transferable
by means of a first optical signal (a) out of first non-reactive state in which the conversion can not be initiated by a physical signal into a reactive state in which the conversion can be initiated by the physical signal, and
by means of at least one of the first and a second optical signal (b) into one of the first non-reactive state and a second non-reactive state,
the method comprising:
forming a converting front of light comprising one of the first optical signal and a combination of the first and second optical signals in the conversion area, wherein the intensity of the light, over a depth of the converting front in the direction of the combined intensity profiles of the first and second optical signals, the depth being smaller than the diffraction limit at the wavelength of the light, increases so steeply that a portion of the substance in the reactive state over the depth of the converting front increases from essentially zero due to transferring the substance (a) out of the first non-reactive state into the reactive state, and
decreases to essentially zero again due to transferring the substance (b) into the one of the first and second non-reactive states;
moving the converting front over the conversion region in a direction opposite to the increase of the intensity of the light over the depth of the converting front; and
applying the physical signal at least to a longitudinal part of the converting front, if the converting front is in selected positions in the conversion region,
wherein the first and second optical signals whose intensities increase over the converting from essentially have no intensity in front of the converting front being sufficient for driving any changes of state of the substance.

20. The method of claim 19, wherein the substance is transferred by means of the first optical signal (a) out of the first non-reactive state into the reactive state and by means of the second optical signal (b) into the one of the first and second non-reactive states, wherein the light includes both the first optical signal and the second optical signal, and wherein the intensity distributions of both the first and second optical signals in the conversion region are structured in a same way by means of same optical elements.

21. The method of claim 19, wherein the physical signal is applied with spatial resolution along the conversion front extending perpendicular to the increase of the intensity of the light.

22. The method of claim 19, wherein effector molecules are released by converting the substance.

23. The method of claim 19, wherein the conversion of the substance is reversible.

24. The method of claim 19, wherein the physical signal is a further optical signal, wherein the substance is arranged in tracks at a distance of at least the diffraction limit at the wavelength of the further optical signal, wherein the converting front is aligned perpendicular to the tracks, and wherein the further optical signal is applied at a spatial resolution differentiating between the tracks.

25. A process of determining the distribution of a substance in a measurement region, the substance being selected from a group of substances which display at least one of the following transfer properties:
the substance, by means of a first optical signal, is transferable (a) out of a first state in which no measurement signal is available from the substance into a measurement state in which a measurement signal is available from the substance,
the substance, by means of at least one of the first optical signal and a second optical signal, is transferable (b) into one of the first state and a second state in
which no measurement signal is available from the substance, the process comprising:
forming a measuring front of light comprising one of the first optical signal and a combination of the first and second optical signals in the measurement region, wherein the intensity of the light, over a depth of the measuring front in the direction of the combined intensity profiles of the first and second optical signals, the depth being smaller than the diffraction limit at the wavelength of the light, increases so steeply that a portion of the substance in the measurement state over the depth of the converting front displays one of the following courses
(i) an increase from essentially zero up to a saturation value due to transferring the substance (a) out of the first state into the measurement state,
(ii) a decrease from a starting value to essentially zero due to transferring the substance (b) into the one of the first and second states in which no measurement signal is available from the substance, (iii) an increase from essentially zero due to transferring the substance (a) out of the first state into the measurement state and a decrease from back to essentially zero due to transferring the substance (b) into the one of the first and second states in which no measurement signal is available from the substance;

moving the measuring front over the measurement region in a direction opposite to the increase of the intensity of the light over the depth of the measuring front;

at least recording the measurement signal emitted out of the measuring front for different positions of the measuring front in the measurement region; and assigning the recorded measurement signal to the corresponding position of the measuring front in the measurement region, wherein the first and second optical signals whose intensities increase over the measuring front essentially have no intensity in front of the measuring front being sufficient for driving any changes of state of the substance.

26. The process of claim 25, wherein a distribution of the measurement signal emitted over the depth of the measuring front is recorded at a spatial resolution along the measuring front extending perpendicular to the increase of the intensity of the light and is assigned to the corresponding positions of the measuring front in the measurement region.

27. The process of claim 25, wherein the substance by means of the first optical signal is transferable both (a) out of the first state in which no measurement signal is available from the substance into the measurement state and (b) into the second state in which no measurement signal is available from the substance, wherein the intensity of the light consisting of the first optical signal, over the depth of the measuring front which is smaller than the diffraction limit at the wavelength of the first optical signal, increases in such a way that the portion of the substance in the measurement state increases from essentially zero, due to transferring the substance (a) out of the first state into the measurement state, and decreases back to essentially zero, due to transferring the substance (b) into the second state.

28. The process of claim 27, wherein the measurement state is an excited electronic state out of which the substance spontaneously emits luminescence light, and wherein the second state is a dark state which has a lifetime longer than a measuring time over which the measurement signal is recorded for one position of the measuring front in the measurement region.

29. The process of claim 28, wherein the substance is transferred into the dark state by further exciting the substance out of the excited electronic state.

30. The process of claim 25, wherein the substance, by means of a switch-on signal is switchable out of an off-state in which the substance is not transferable into the measurement state into an on-state in which the substance is transferable into the measurement state, wherein a certain portion of the substance which is present at a higher absolute concentration in the on-state in the measurement region is adjusted by means of the switch-on signal.

31. The process of claim 25, wherein the first optical signal is a switch-on signal switching the substance out of the first state in which it is not excitable for emission of luminescence light into the measurement state in which it is excitable for the emission of the luminescence light and wherein an excitation signal which excites the substance in the measurement state for the emission of the luminescence light is additionally applied to the measurement region, the luminescence light being recorded as the measurement signal.

32. The process of claim 25, wherein the measuring front is straight.

33. The process of claim 25, wherein the measuring front spans at least hundred times the diffraction limit at the wavelength of the light of which the measuring front is formed.

34. The process of claim 25, wherein the measuring front covers a full width of the measurement region.

35. The process of claim 25, wherein the measurement signal is recorded at a temporal resolution for each position of the measuring front in the measurement region.

36. The process of claim 25, wherein the distribution of the measurement signal emitted over the depth of the measuring front is recorded with a line detector aligned in width direction of the measuring front.

37. The process of claim 25, wherein the distribution of the measurement signal out of the entire measurement region is recorded with a detector array.

38. The process of claim 25, wherein the intensity of the light increases over a depth of the measuring front which is smaller than half of the diffraction limit at the wavelength of the light so that the transfer of the substance (a) into the measurement state increases from essentially zero and the transfer of the substance (b) out of the measuring state into the one of the first and second states increases to essentially completely.

39. The process of claim 25, wherein the measuring front is moved in at least two linearly independent directions over the measurement region, wherein the distribution of the measurement signal emitted over the depth of the measuring front is recorded with spatial resolution along the measuring front.

40. The process of claim 39, wherein the substance in the measurement region over which the measuring front has already been moved is subjected to a resetting optical signal prior to moving the measuring front again over the measurement region.

41. The process of claim 40, wherein the resetting optical signal is an optical signal of the blue to ultraviolet wavelength range.

42. The process of claim 25, wherein the substance is arranged in tracks at a distance of at least a diffraction limit at the wavelength of the measurement signal and wherein the measuring front is aligned perpendicular to the tracks.

43. The process of claim 42, wherein the distribution of the substance in the tracks is determined for reading information from a data carrier comprising the tracks.

\* \* \* \* \*